(12) United States Patent
Houle et al.

(10) Patent No.: US 6,709,417 B1
(45) Date of Patent: *Mar. 23, 2004

(54) VALVE FOR INTRAVENOUS-LINE FLOW-CONTROL SYSTEM

(75) Inventors: Philip Houle, Menlo Park, CA (US); William T. Larkins, Manchester, NH (US); Richard Lanigan, Concord, NH (US)

(73) Assignee: DEKA Products Limited Partnership, Manchester, NH (US)

(*) Notice: Subject to any disclaimer, the term of this patent is extended or adjusted under 35 U.S.C. 154(b) by 41 days.

This patent is subject to a terminal disclaimer.

(21) Appl. No.: 09/715,246

(22) Filed: Nov. 17, 2000

Related U.S. Application Data

(60) Division of application No. 08/917,537, filed on Aug. 22, 1997, now Pat. No. 6,165,154, which is a continuation-in-part of application No. 08/478,065, filed on Jun. 7, 1995, now Pat. No. 5,755,683.

(51) Int. Cl.[7] .................................................. A61M 1/00
(52) U.S. Cl. .......................................... 604/153; 604/34
(58) Field of Search .............................. 604/6.1, 9, 246, 604/247, 256, 257, 30, 32, 34; 251/206, 208

(56) References Cited

U.S. PATENT DOCUMENTS

| | | | |
|---|---|---|---|
| 1,792,906 A | 2/1931 | Neilos | 251/209 |
| 2,526,017 A | 10/1950 | Figg | 251/209 |
| 2,902,253 A | 9/1959 | Page | 251/209 |
| 3,540,694 A | 11/1970 | Cornelius | 251/209 |
| 3,722,858 A | 3/1973 | Sugimoto et al. | 251/209 |
| 3,727,882 A | 4/1973 | Burris et al. | 251/209 |
| 4,230,300 A | 10/1980 | Wiltse | 251/205 |
| 4,648,868 A | 3/1987 | Hardwick et al. | 604/32 |
| 4,667,927 A | 5/1987 | Oscarsson | 251/209 |
| 4,807,660 A | 2/1989 | Aslanian | 137/382 |
| 5,005,604 A | 4/1991 | Aslanian | 137/556 |
| 5,045,068 A | 9/1991 | Kawai et al. | 604/246 |
| 5,088,515 A * | 2/1992 | Kamen | 137/15.17 |
| 5,113,904 A | 5/1992 | Aslanian | 137/556 |
| 5,156,186 A | 10/1992 | Manska | 137/556 |
| 5,193,990 A | 3/1993 | Kamen et al. | 417/474 |
| 5,241,985 A | 9/1993 | Faust et al. | 137/505.13 |
| 5,364,371 A | 11/1994 | Kamen | 604/251 |
| 5,378,126 A | 1/1995 | Abrahamson et al. | 417/479 |
| 5,584,671 A | 12/1996 | Schweitzer, Jr. et al. | 417/298 |
| 5,649,810 A | 7/1997 | Schweitzer, Jr. et al. | 417/298 |
| 5,816,779 A | 10/1998 | Lawless et al. | 417/63 |
| 6,364,857 B1 * | 4/2002 | Gray et al. | 604/153 |

FOREIGN PATENT DOCUMENTS

| | | |
|---|---|---|
| BE | 535179 | 2/1955 |
| DE | 58977 | 11/1890 |
| EP | 0 222 088 A2 | 5/1987 |

(List continued on next page.)

*Primary Examiner*—Manuel Mendez
*Assistant Examiner*—Mark K. Han
(74) *Attorney, Agent, or Firm*—Bromberg & Sunstein LLP

(57) ABSTRACT

A valve (7) for use in controlling the flow of IV fluid from a source to a patient. A cassette may include along the fluid passage through the cassette, first and second membrane-based valves (6, 7) on either side of a pressure-conduction chamber (50), and a stopcock-type valve (20). The stopcock valve is preferably located downstream of the second membrane-based valve (7), which is preferably located downstream of the pressure-conduction chamber (50). The membrane defining the valving chamber of the second membrane-based valve (7) is preferably large and resilient, so that the valving chamber(75) may provide a supply of pressurized intravenous fluid to the patient, when the valve (6) is closed and the stopcock valve (20) provides a restriction downstream of the valve (7). The pressure-conduction chamber (50) preferably has a membrane (41) that is stable in the empty-chamber position but relatively unstable in the filled-chamber position.

8 Claims, 14 Drawing Sheets

FOREIGN PATENT DOCUMENTS

| | | |
|---|---|---|
| EP | 0 293 592 | 12/1988 |
| FR | 2138617 | 3/1972 |
| FR | 2340491 | 2/1976 |
| GB | 2 053 378 A | 2/1981 |
| WO | WO 92/16304 | 10/1992 |
| WO | 93/23096 | 11/1993 |
| WO | 94/27669 | 12/1994 |

* cited by examiner

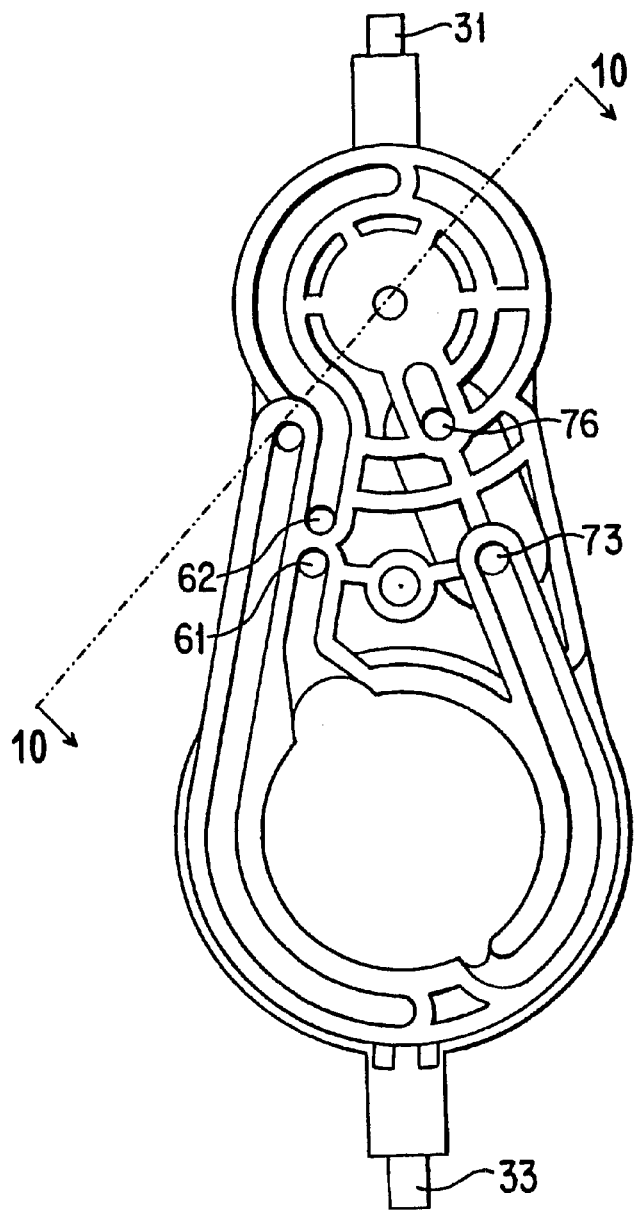 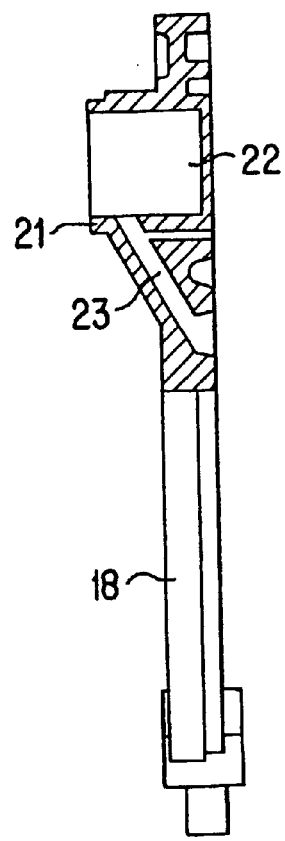
FIG. 9
FIG. 10

VALVE FOR INTRAVENOUS-LINE FLOW-CONTROL SYSTEM

RELATED APPLICATIONS

The present application is a divisional of U.S. application Ser. No. 08/917,537 filed Aug. 22, 1997, now U.S. Pat. No. 6,165,154 which, in turn, is a continuation-in-part of U.S. application Ser. No. 08/478,065 filed Jun. 7, 1995, which issued as U.S. Pat. No. 5,755,683 on May 26, 1998, which was concurrently filed with applications Ser. No. 08/472,212, entitled "Intravenous-Line Flow-Control System" for an invention by Heinzmann, Kamen, Lanigan, Larkins, Lund and Manning, which issued on Jun. 30, 1998 as U.S. Pat. No. 5,722,637; Ser. No. 08/481,606, entitled "Intravenous-Line Air-Elimination System" for an invention by Manning, Larkins, Houle, Kamen and Faust, which issued on Feb. 3, 1998 as U.S. Pat. No. 5,713,865; and Ser. No. 08/477,380, entitled "Intravenous-Line Air-Detection System" for an invention by Larkins, Beavis and Kamen, which issued on Jun. 24, 1997 as U.S. Pat. No. 5,641,892. All of these related applications are hereby incorporated herein by reference.

TECHNICAL FIELD

The present invention relates to apparatus and methods for controlling flow through an intravenous line.

SUMMARY OF THE INVENTION

The invention is directed to a cassette for controlling the flow of IV fluid from a source to a patient. The cassette preferably includes, along the fluid passage through the cassette, first and second membrane-based valves on either side of a pressure-conduction chamber, and a stopcock-type valve. The stopcock valve is preferably located downstream of the second membrane-based valve, which is preferably located downstream of the pressure-conduction chamber.

In a preferred version of the cassette, which is primarily made out of rigid material, the membrane for the second membrane-based valve is disposed adjacent the housing, such that the rigid housing and the membrane define a valving chamber. One passage enters the valving chamber at a first mouth located at the end of a protrusion of the rigid housing into the valving chamber towards the membrane, and the valve may prevent the flow of fluid therethrough when the membrane is forced against the first mouth, by the control unit. The control valve restricts the flow of intravenous fluid from the valving chamber to the patient, since it is located downstream of the valving chamber. The membrane defining the valving chamber is preferably large and resilient, so that the valving chamber may provide a supply of pressurized intravenous fluid to the patient, when the first mouth is sealed closed and when there is a restriction downstream of the valving chamber.

For the pressure-conduction chamber, a membrane is preferably disposed adjacent the rigid housing, so as to define a pressure-conduction chamber, wherein the rigid housing portion that defines the pressure-conduction chamber is generally dome-shaped. The membrane has a filled-chamber position, in which position the pressure-conduction chamber is substantially at its greatest volume, and an empty-chamber position, in which position the pressure-conduction chamber is at its smallest volume, and in which position the membrane rests against the rigid housing and assumes the dome shape of the rigid housing. The membrane preferably has a structure for creating instability in the membrane in the filled-chamber position. Preferably, this structure may be actuated to create instability in the membrane in the empty-chamber position. The rigid housing and the second membrane in the empty-chamber position preferably define an unobstructed fluid passageway through the pressure-conduction chamber from the first to the second pressure-conduction chamber mouth. Preferably, the structure for creating instability in the membrane causes the membrane, when its at its full-chamber position, to collapse in the region of the pressure-conduction chamber's outlet mouth before collapsing nearer the inlet mouth. This structure helps force bubbles in the fluid upward toward the inlet mouth and the IV fluid source during a bubble-purge cycle.

BRIEF DESCRIPTION OF THE DRAWINGS

FIGS. 8 and 9 show side and rear views respectively of the middle panel of FIG. 7.

FIG. 10 shows a partial cross-section of the middle panel of FIG. 7.

DETAILED DESCRIPTION OF SPECIFIC EMBODIMENTS

Figure 1:
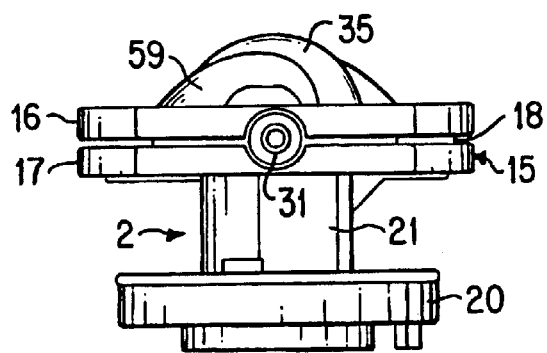
FIG. 1 shows a top view of a cassette according to a preferred embodiment of the present invention.
Figure 3:
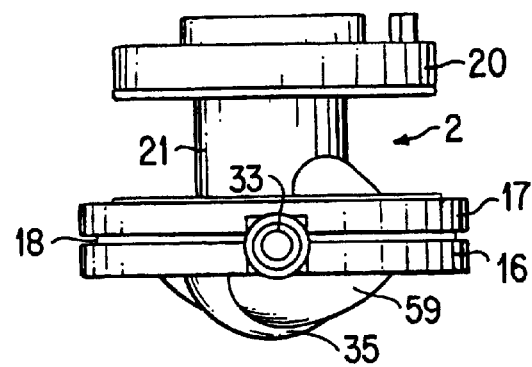
FIGS. 2 and 3 show front and bottom views respectively of the cassette of FIG. 1.
Figure 2:
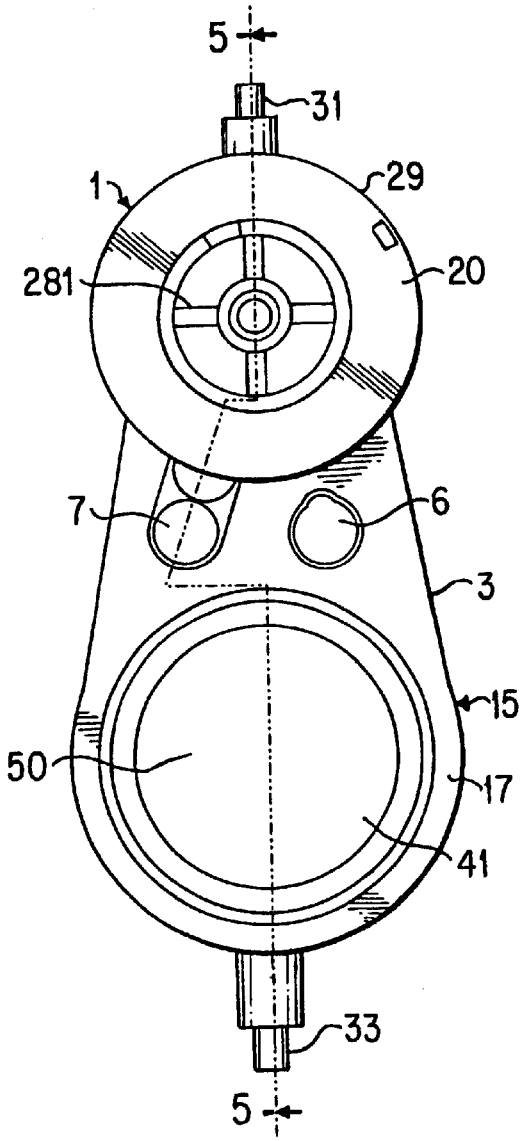
Figure 4:
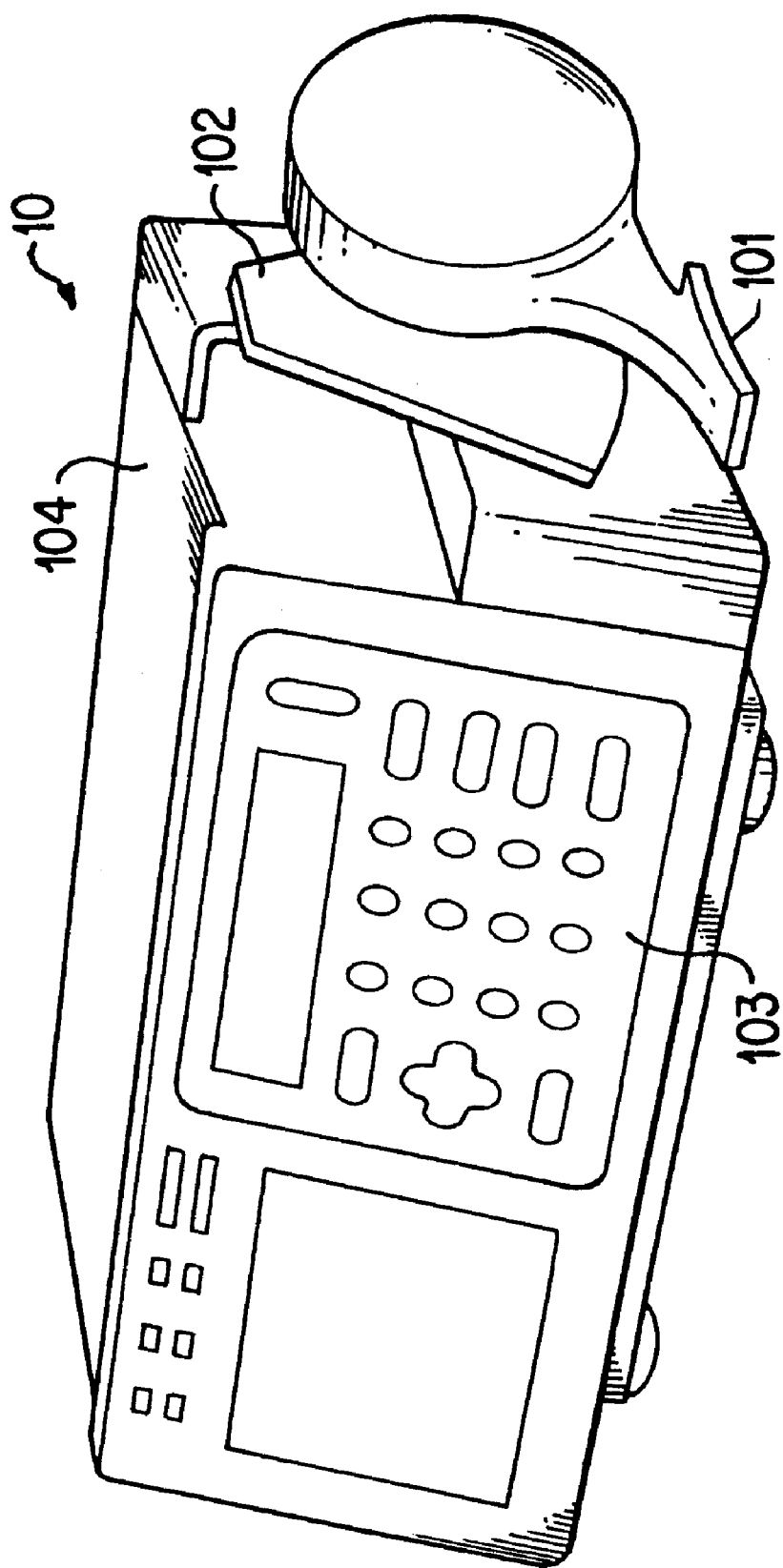
FIG. 4 shows a control unit for receiving and controlling a cassette, such as the cassette of FIGS. 1–3.

The present invention includes a cassette for use in a system for controlling the flow of IV fluid to a patient, along the lines of the cassettes disclosed in U.S. Pat. Nos. 5,088,515 and 5,195,986. A preferred embodiment of the cassette is depicted in FIGS. 1–3, which respectively depict top, front and bottom views of the cassette. The cassette is used in a control unit, such as that described in above-referenced U.S. Pat. No. 5,772,637, entitled "Intravenous-Line Flow-Control System," which is similar to the control unit described in U.S. Pat. No. 5,088,515, which describe the use of pressure, preferably pneumatic pressure, for controlling the actuation of valves and the urging of fluid into and out of a pressure-conduction chamber. In addition to performing the function of a pump urging fluid through the IV line, the pressure-conduction chamber can measure the amount of IV fluid being delivered to the patient as well as detect the presence of bubbles in the IV fluid in the pressure-conduction chamber. Preferred methods of detecting and eliminating air bubbles from the IV fluid are discussed in the above-referenced patent applications for "Intravenous-Line Air-Detection System" and "Intravenous-Line Air-Elimination System," now U.S. Pat. Nos. 5,641,982 and 5,713,865, respectively. FIG. 4 depicts a preferred version of a control unit 10. Control unit 10, which has a user-interface panel 103 containing a key pad and a display so that the status of the IV fluid delivery may be monitored and modified by medical personnel. The cassette is slipped behind door 102, and by turning handle 101 the door is pressed against the cassette, which in turn is then pressed against the main housing of the control unit 10. The main housing 104 preferably includes mechanical means for actuating membrane-covered valves and for applying a pressure against the membrane of the pressure-conduction chamber. The main housing 104 also includes means for turning the control wheel of the cassette.

Referring to FIG. 2, the main components of the preferred embodiment of the cassette are a first membrane-based valve 6, a pressure-conduction chamber 50, a second membrane based valve 7 and a stopcock-type control valve 20. Valve 6 controls the flow to the pressure-conduction chamber 50 from the inlet 31 to the cassette, which is connected to an IV line, which in turn is connected to a source of IV fluid. The second membrane-based valve 7 and the control valve 20 together are used to control the flow of fluid from the pressure-conduction chamber 50 to the outlet to the cassette 33, which is connected to the IV line leading to the patient.

Figure 25:
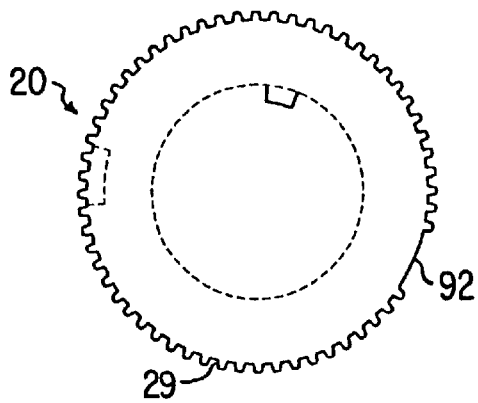
FIG. 25 shows a preferred arrangement of teeth around the circumference of the control wheel.

The rigid housing 15 of the cassette is made primarily from three rigid panels. A front panel 17, a middle panel 18, and a rear panel 16, all three of which can be seen in FIGS. 1 and 3. The front panel is preferably molded integrally with the outer collar 21 of the control valve 2. The wheel 20 of the control valve 2 preferably includes ribs 281 and/or teeth mounted along the circumference 29 of the knob 20. (FIG. 25 shows a preferred arrangement of teeth around the circumference 29 of the control knob 20.) The teeth and/or ribs 281 may be engaged by the main housing 104 of the control unit 10, so that the control unit 10 may change the resistance that the control valve 2 exerts on the IV fluid passing through the valve.

Figure 5:
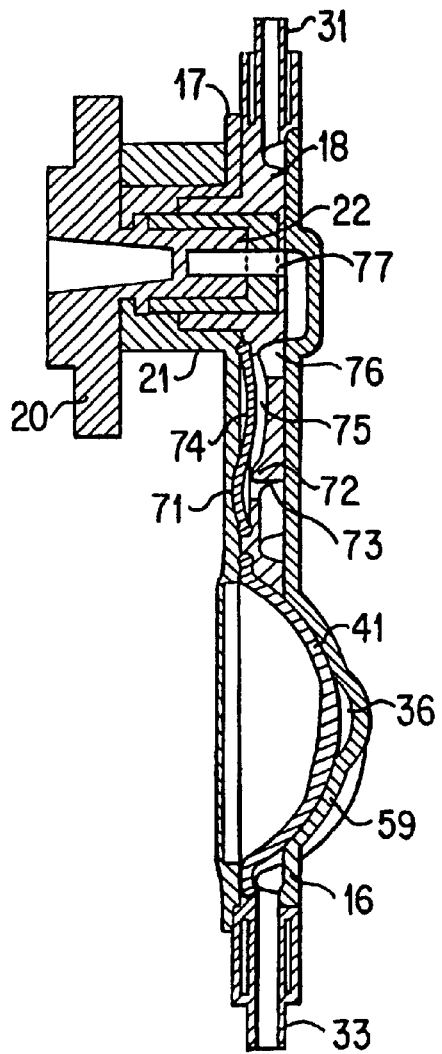
FIG. 5 shows a cross-section of the cassette of FIGS. 1–3.
Figure 6:
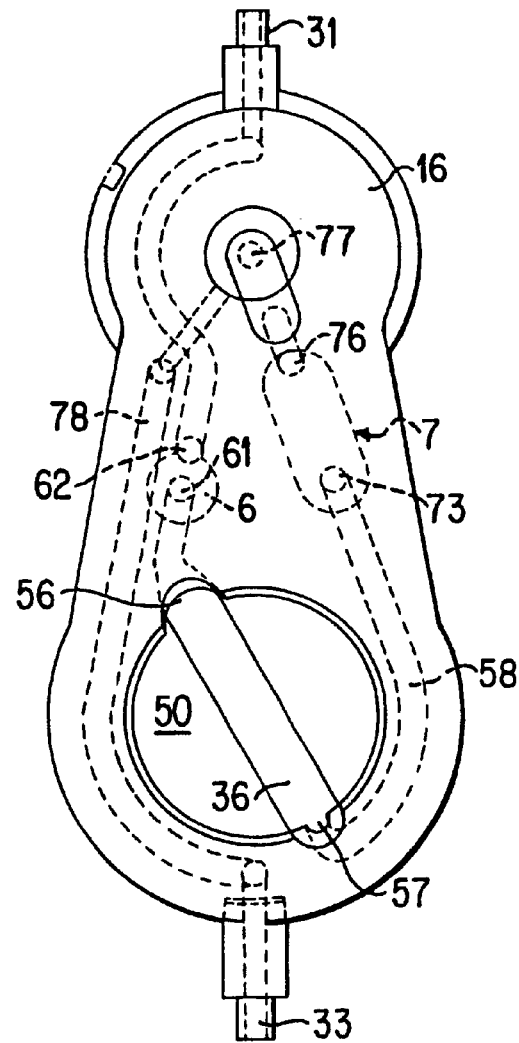
FIG. 6 shows a rear view of the cassette and shows the fluid paths through the cassette.

The cassette may also be used without the control unit 10. In that case, the control wheel 20 may be turned by hand. When disengaged from the control unit 10, the membrane of the pressure-conduction chamber 50 is preferably collapsed so that it rests against the rigid rear wall 59 of the pressure-conduction chamber 50. With the membrane in this collapsed state, IV fluid may still easily flow through the pressure-conduction chamber 50 through a raised portion 35 of the rear wall 59. This raised portion 35 defines a conduit 36 leading from the inlet mouth of the pressure-conduction chamber 50 to the outlet mouth of the pressure-conduction chamber, as can be seen in FIG. 6. FIG. 6 shows the fluid paths leading through the cassette. As noted above, fluid enters the cassette through the inlet 31, whence it flows through a fluid path to valve 6. The fluid then enters the valving chamber of valve 6 through an inlet port 62. An outlet port 61 is preferably mounted on a protrusion so that pressure from the pressure-conduction chamber 50 is less likely to force the membrane to lift from the outlet port 61. From valve 6 the fluid passes to the inlet mouth 56 of the pressure-conduction chamber 50. The pressure-conduction chamber is seen in the cross-sectional view of FIG. 5. A membrane 41 allows pressure from the control unit 10 to be applied to the fluid in the pressure-conduction chamber 50 without the fluid coming into contact with the control unit 10. When the membrane 41 is in its collapsed position resting against rigid wall 59, as shown in FIG. 5, fluid can still pass from inlet valve 56 through conduit 36 to the outlet valve 57. After passing through the pressure-conduction chamber 50, the fluid flows to the second membrane-based valve 7, which included an inlet mouth 73, which is mounted on a protrusion 72 in similar fashion to the outlet port 61 of the first membrane-based valve 6. The second membrane-based valve's inlet mouth 73 and the protrusion 72 on which it is mounted can be seen in the cross-sectional view of FIG. 5. Like the outlet port 61 of the first membrane-based valve, the inlet mouth 73 may be closed by the application of pressure by the control unit on a membrane; a first portion 71 of the membrane that closes off the inlet mouth 73 can be seen in FIG. 5. After passing through the outlet mouth 76 of the second membrane-based valve 7, the fluid passes to the inlet 77 of the stopcock-type control valve, which inlet can be seen in both FIGS. 5 and 6. After passing through the control valve and the fluid path 78 exiting from the control valve, the fluid passes to the outlet of the cassette 33 and to the IV line leading to the patient.

Figure 7:
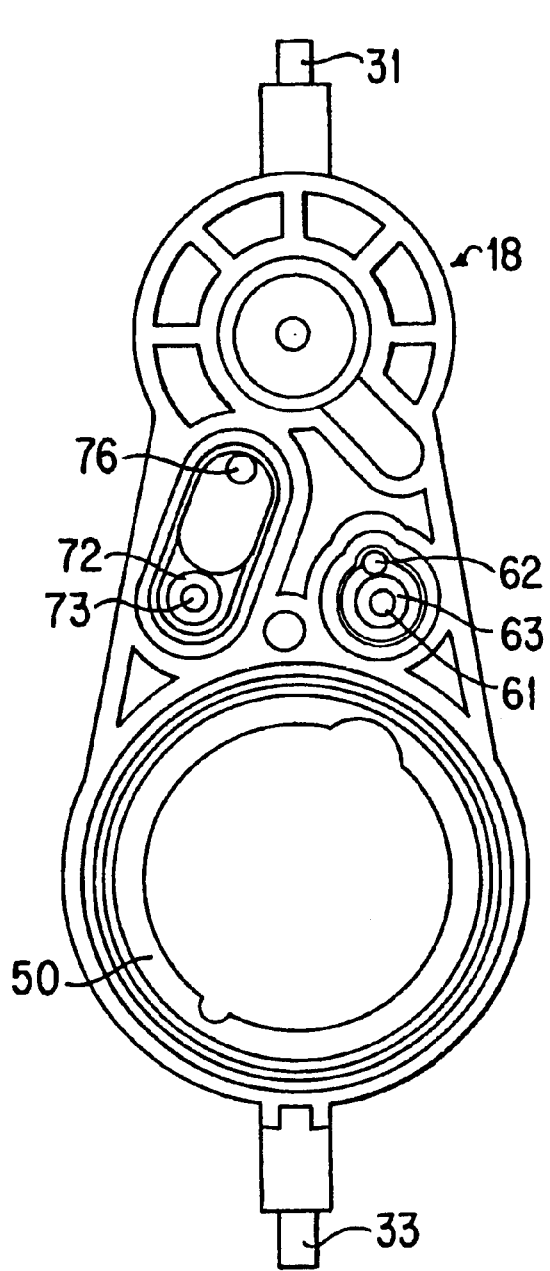
FIG. 7 shows a front view of the middle rigid panel of the cassette of FIGS. 1–3.
Figure 8:
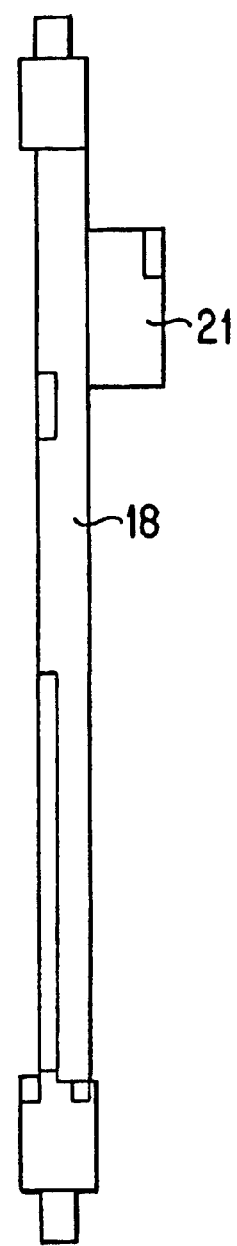

FIG. 7 shows a front view of the rigid middle portion of the cassette, and FIG. 8 shows a side view of the middle rigid panel 18. The middle rigid panel 18 defines the cassette inlet 31 and outlet 33, a circumferential portion of the pressure-conduction chamber 50, and port 62, outlet port 61, inlet mouth 73, and outlet mouth 76 of the two membrane-based valves 6 and 7. The protrusions 63 and 72 of the outlet port 61 and inlet mouth 73 can also be seen in FIG. 7. FIG. 9 shows a rear view of the middle rigid panel 18 shown in FIGS. 7 and 8. The ports/mouths 61, 62, 73, 76 can also be seen in FIG. 9. FIG. 10 shows a partial cross-section of the middle rigid portion. The cross-section shows the outer collar 21 of the control valve, which is integrally molded with the rest of the middle rigid portion. The outer collar 21 defines a hollow area 22 and a fluid path 23 leading from the hollow area 22.

Figure 11:
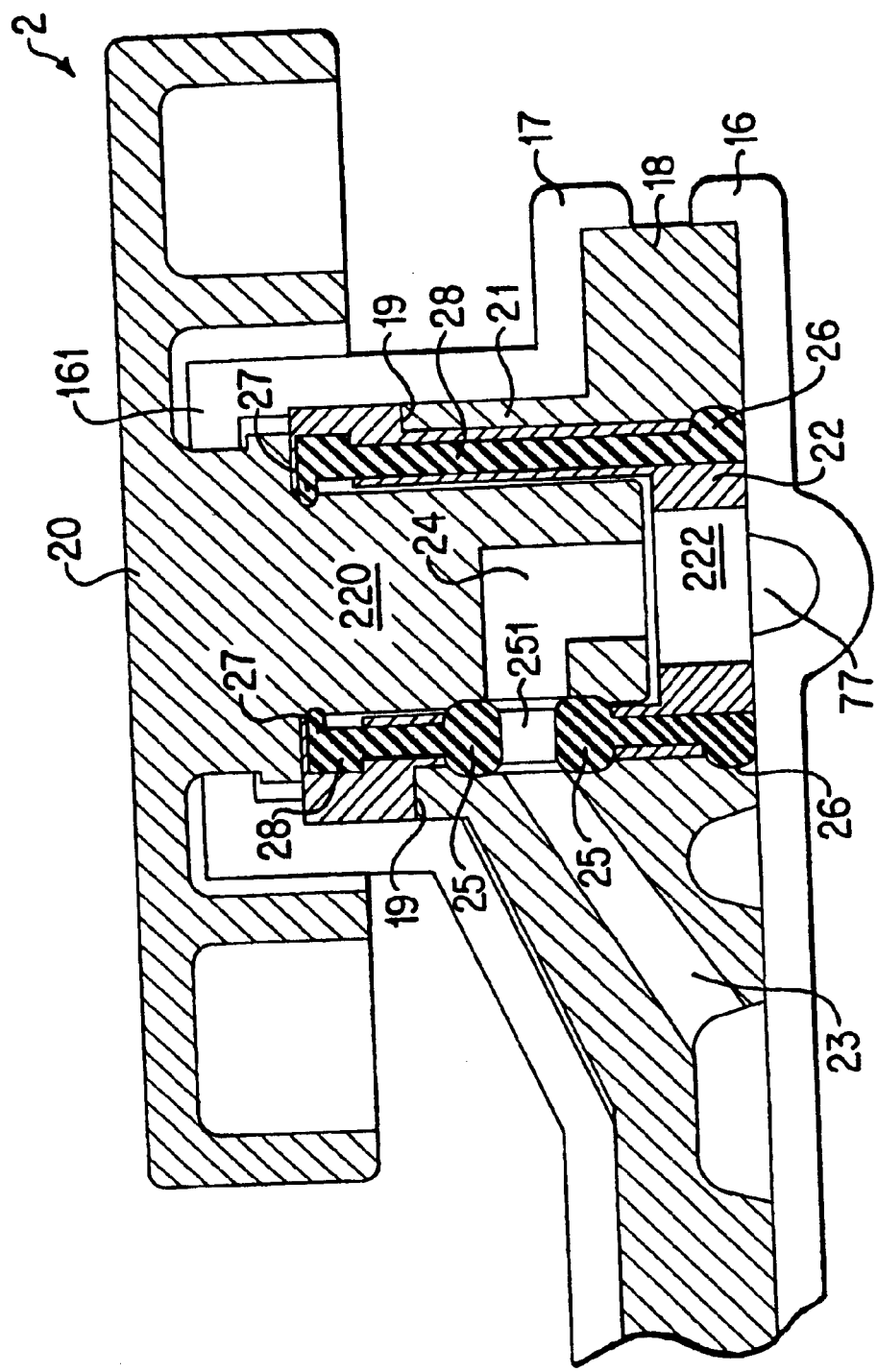
FIG. 11 is a cross-sectional detail of the control valve of the cassette according to a preferred embodiment of the invention.
Figure 12:
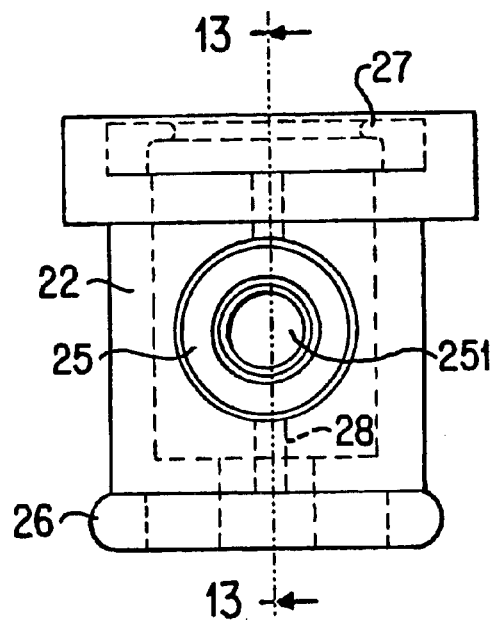
FIG. 12 shows a side view of an outer cylinder (a valve-seat member) having rigid and resilient elements that may be used in the control valve.
Figure 13:
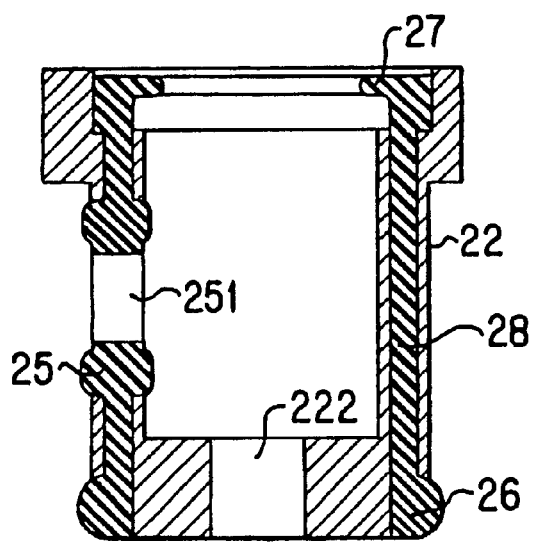
FIG. 13 shows a cross-sectional view of the cylinder of FIG. 12.

FIG. 11 shows a cross-section of an assembled control valve 2 that may be used in a cassette according to the present invention. Just inside of the outer collar 21 is a valve-seat member 22 fixedly attached to the outer collar 21 so that the valve-seat member 21 does not rotate with respect to the rest of the cassette. The valve-seat member 21 is depicted in greater detail in FIG. 12 and in cross-section in FIG. 13. The valve-seat member 22 also defines a hollow area, which accepts the shaft 220 of the control wheel 20, so that the control wheel's shaft 220 rotates with the control wheel 20. The valve-seat member 22 is comprised mostly of rigid material, but importantly it also includes molded-over resilient material, which is used to form sealing O-rings. This resilient material forms an O-ring 26 around the base of the valve-seat member 22; the rigid portion of the base defines a passage 222, connecting the valve inlet 77 to passage 24. The resilient material 25 also provides a seal around an aperture 251 in the circumferential surface of the member 22. At the end of the member 22 opposite the inlet passage 222 is an inner O-ring 27 which forms the seal between the control wheel's shaft 220 and the valve-seat member 22. The O-ring 26 around the exterior circumference of the base provides a seal between the outer circumferential wall of the valve-seat member 22 and the inner circumferential wall of the outer collar 21. Likewise, the O-ring 25 around the circumferential port 251 may provide a seal between the outer circumferential wall of the valve-seat member 22 and the inner circumferential wall of the outer collar 21. Together, O-rings 25, 26 prevent fluid from leaking between the valve-seat member 22 and the outer collar 21. Importantly, the O-ring 25 of port 251 also provides a seal between the valve-seat member 22 and the shaft 220, so that when the valve is in the fully closed position no flow is permitted between passageway 24 of shaft 220 and the port 251 of the valve-seat member 22.

The advantage of this design over previous stopcock valves is that the outer diameter of the shaft 220 may be slightly less than the inner diameter of the valve-seat member 22, whereas previous stopcock valves required an interference fit between the inner and outer components. It will be appreciated that the stopcock valve of the present invention may use frusto-conical-shaped members instead of cylindrical members. The interference fit of prior-art devices created a great deal of resistance when the stopcock valves were turned. The use of O-rings in the stopcock valve of the present invention avoids the need for this interference fit and the greater torque required for turning the valve resulting from the interference fit. O-ring 27 prevents leaking from the space between the valve-seat member 22 and the shaft of the control wheel 20.

The valve-seat member is preferably made in a two-part molding process, wherein the rigid portion is first molded and then the softer resilient material is over-molded onto the rigid portion. Channels may be provided in the initially molded rigid portion so that the resilient material may flow to all the desired locations; this results in columns of resilient material 28 connecting the areas of resilient material through these channels. The valve-seat member 22 is preferably molded separately from the rest of the cassette, and when the cassette is assembled the valve-seat member 22 is placed in the hollow defined by the outer collar 21 of the middle panel 18, and aligned so that aperture 251 lines up with passageway 23. (The shape of the outer diameter of the valve-seat member 22 and the inner diameter of the outer collar 21 may be complementarily shaped so that the valve-seat member must align properly with the aperture 251 and the passageway 23 lined up.) Then, the front rigid panel 17 is ultrasonically welded (along with the rear rigid panel 16) to the middle rigid panel 18, and the valve-seat member 22 is then held in place in the hollow area defined by the outer collar 21. The outer circumference of the valve-seat member 22 may be a bit smaller than the inner diameter of the outer collar 21; O-rings 25, 26 prevent fluid from flowing from the passages 77 or 23 to point 19. This design of the valve-seat member 22 avoids the need for tight tolerances in the various components of the valve 2. The control wheel's shaft 220 may be inserted into the hollow area defined by valve-seat member 22 after the rest of the valve has been assembled. The shaft 22(0 is held in place by a lip 161around the inner circumference of the hollow area defined by the rear rigid panel 16

Figure 14:
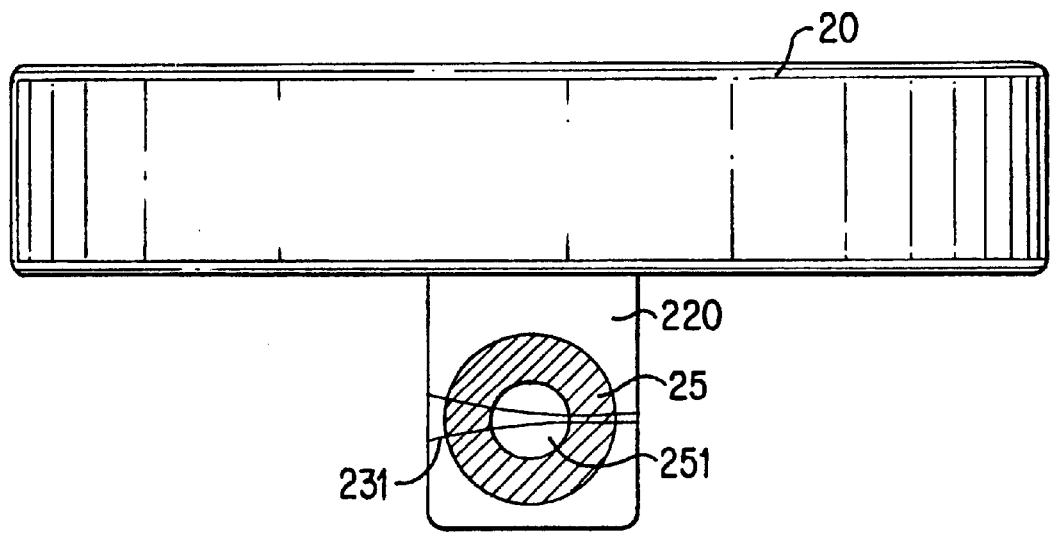
FIG. 14 depicts the relationship between the aperture of the FIG. 12 cylinder and the groove used in the control valve.

When the valve 2 is fully opened, the circumferential aperture 251 is lined up with the fluid passage 24 in the shaft 220. When the valve is fully closed there is no fluid communication between the aperture 251 and the fluid passage 24. The outer circumferential surface of the shaft 220 preferably includes a groove extending circumferentially around the shaft's outer circumferential wall from the terminus of the fluid passage 24 at the outer circumferential wall; the groove tapers in cross-sectional area and does not extend all the way around the outer circumference of the shaft 220. The groove provides greater control of the flow rate. FIG. 14 shows the respective locations of the groove 231, which is located on the outer circumference of the shaft 220 and the circumferential aperture 251 of the valve seat member 22. As the aperture 251 rotates to the right, in the FIG. 14 perspective, the resistance to flow increases, until the groove 231 tends and the aperture 251 loses fluid communication with the groove 231, at which point flow is completely shut off through the control valve 2. As the aperture 251 rotates to the left, in the FIG. 14 perspective, the resistance to flow decreases. Preferably, the groove 231 is longer than the diameter of the aperture 251, so that the flow rate may be controlled more finely.

As noted above, the cassette may be used independently of the control unit 10. When the cassette is used in this manner it is preferable that the membrane 41 rest against the rigid back 59 of the pressure-conduction chamber 50 so as to minimize the volume of the conduit 36 for fluid passing through the pressure conduction chamber 50. If the membrane 41 were too flexible and the volume of the pressure-conduction chamber 50 varied widely, medical personnel would be unable to rely on a quick visual inspection of the rate of dripping in the drip chamber to indicate a steady, desired flow rate through the IV line. Thus, it is desired that the structure of the membrane 41 be such that it tends to rest against wall 59 unless and until a sufficient pressure differential is created across the diaphragm 41. This pressure differential is preferably caused by a negative gas pressure caused by the control unit 10. Although it is desired to manufacture the diaphragm 41 so that it has some tendency to rest against wall 59, it is desired to make the diaphragm 41 floppy in the other direction so that less pressure is required to move it from its position when the pressure-conduction chamber 50 is full, the "filled-chamber" position. It is also desired that the measurement gas provided by the control unit 10 against the outer face of the membrane 41 be at substantially the same pressure as the fluid on the inner side of the membrane 41 in the pressure-conduction chamber 50.

Figure 15:
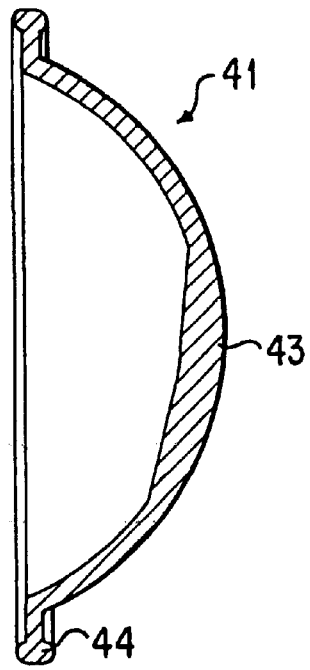
FIG. 15 shows a cross-sectional view of the membrane that may be used in the pressure-conduction chamber of the cassette shown in FIG. 1.
Figure 16:
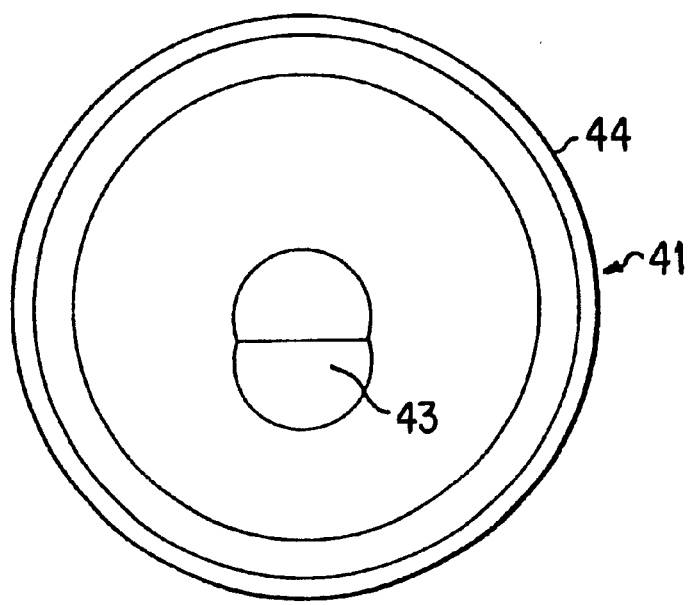
FIGS. 16 and 17 show front and rear views respectively of the FIG. 15 membrane.
Figure 17:
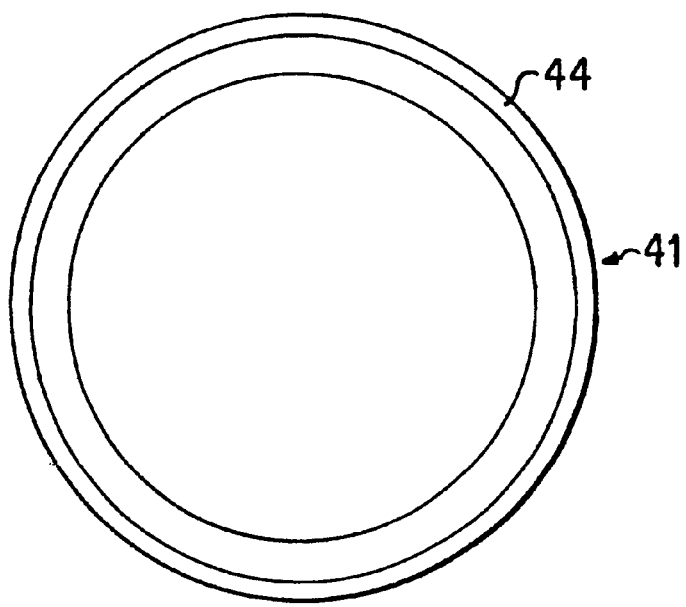

By molding the diaphragm 41 in the shape of a dome corresponding to that of the rigid wall 59, the diaphragm will have a tendency to remain in its position, as shown in FIG. 5, resting against wall 59 when the chamber 50 is at its lowest volume, the "empty-chamber" position. However, when the diaphragm 41 is molded in this way, it also tends to remain in the filled-chamber position, in other words, when the diaphragm 41 is bulging convexly outward from the cassette. This convex, filled-chamber position can be made unstable by adding additional material on the outer, usually concave surface of the diaphragm 41. This additional material 43 can be seen in the cross-section of a preferred embodiment of the diaphragm as shown in FIG. 15. The diaphragm 41 shown in FIG. 15 is molded in the position shown and has a tendency to remain in that position. When the chamber is filled with fluid, the normally concave side of the diaphragm becomes convex, and the additional material 43 is subject to an additional amount of strain since it is at the outer radius of this convex, filled-chamber position. The diaphragm 41 shown in FIG. I5 also includes an integrally molded O-ring 44 around its circumference for mounting and sealing the diaphragm 41 in the cassette. FIG. 16 shows a view of the exterior side of the diaphragm 41 of FIG. 15. This surface of the diaphragm 41 is normally concave when the diaphragm is in the empty-chamber position. The additional material 43 can be seen in the view of FIG. 16. FIG. 17 shows the interior side of the diaphragm 41 of FIG. 15. This side is normally convex when the diaphragm 41 is in the empty-chamber position. Thus, as a result of molding the diaphragm so that its inner surface has a smooth constant radius and the outer surface has additional material, which thereby interrupts the smoothness and constant radius of the rest of the outer face of the diaphragm, the diaphragm 41 has the desired tendency to remain in the empty-chamber position while being unstable in the filled-chamber position.

By positioning this additional material 43 near the outlet mouth 57 of the pressure-conduction chamber 50, the collapse of the diaphragm 41 from its filled-chamber can be somewhat controlled so that the diaphragm tends to collapse first in the lower portion of the pressure-conduction chamber near the outer mouth 57 before further collapsing in the upper region of the pressure conduction chamber nearer the inlet mouth 56. The cassette is preferably mounted in the control unit with a slight tilt so that the passage 36 is vertical and the inlet mouth 56 is at the very top of the chamber 50 and the outlet mouth 57 is at the very bottom of the chamber 50. This orientation permits the bubbles that may be present in the chamber 50 to gravitate towards the inlet mouth 56, which is at the top of the chamber. In a preferred method of eliminating the bubbles from the IV fluid, as described in the above-referenced, concurrently filed application for "Intravenous-Line Air-Elimination System," any bubbles that are detected by the control unit in the pressure conduction chamber 50 are forced by pressure from the control unit against the external surface of the membrane 41 up to the inlet mouth 56 to the cassette inlet 31 up the IV line to the fluid source, sometimes after several purging and filling cycles. When purging the bubbles from the chamber 50 through the inlet mouth 56 it is preferred that the chamber collapse at its bottom first so that the membrane does not interfere with bubbles moving upwards through the chamber 50.

Thus, the additional material 43 creates an instability in the membrane 41 when the membrane is in the filled-chamber position, thereby making the membrane more likely to collapse from the filled-chamber position than a membrane that did not have the additional material. The additional material 43, however, does not create an instability in the membrane 41 when the membrane is in the empty-chamber position. In many situations it is desirable to be able to introduce some instability into the membrane when the membrane is in the empty-chamber position. By introducing such instability into the membrane, less negative pressure is needed to move the membrane from its empty-chamber position.

Figure 26:
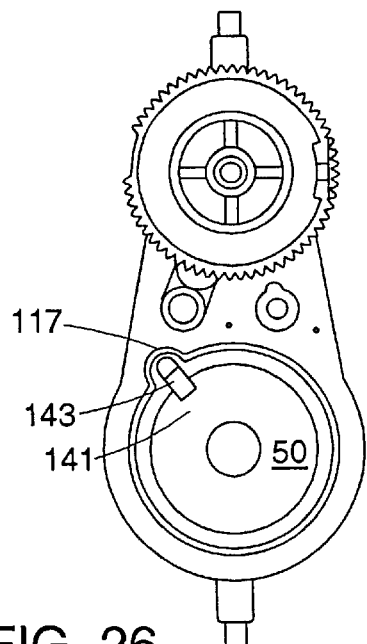
FIG. 26 shows a front view of a cassette according to an alternative preferred embodiment of the present invention.
Figure 27:
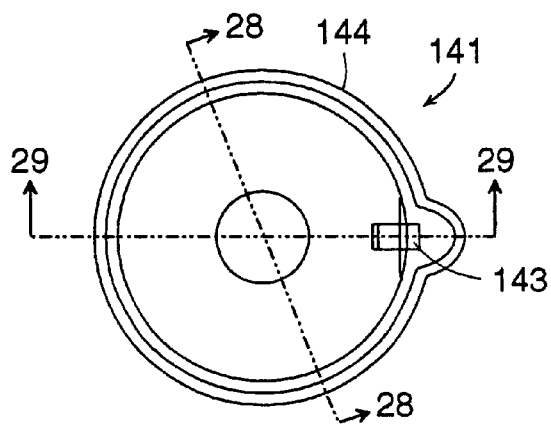
FIG. 27 shows a front view of the membrane that may be used in the pressure-conduction chamber of the cassette shown in FIG. 26.
Figure 28:
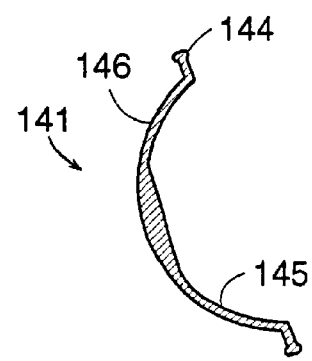
FIG. 28 shows a cross-sectional view of the membrane shown in FIG. 27 along line B—B.
Figure 29:
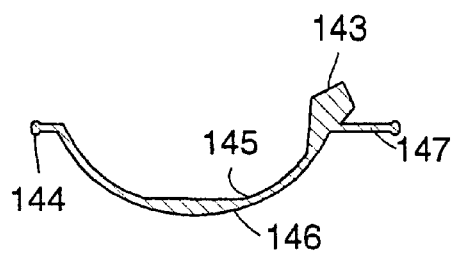
FIG. 29 shows a cross-sectional view of the membrane shown in FIG. 27 along line 29.
Figure 30:
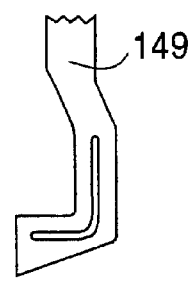
FIG. 30 shows a cross-sectional view of the membrane shown in FIG. 27 along line A—A.

To create an instability in the empty-chamber position, a pressure-relief tab 143 may be added to the membrane 141 as shown in FIG. 26. The pressure-relief tab 143 extends from the exterior surface 145 near the edge of the membrane 141, as can be seen in the cross-sectional view of FIG. 29. FIG. 28 shows another cross-sectional view, which view does not pass through the pressure-relief tab 143, and FIG. 27 shows a front view of the membrane 141. The tab 143 may be actuated by an actuator 149 (shown in FIG. 30) mounted in the control unit. When it is desired to introduce instability into the membrane—which will typically be whenever it is desired to fill a previously empty chamber 50—the actuator 143 forces the tab 143 towards the O-ring 144. This action pulls the portion of the membrane 141 near the tab 143 away from the cassette's rigid wall, which partially defines the pressure-conduction chamber 50. The tab 143 is located near the inlet mouth of the chamber 50 so that, when the actuator 149 pulls a portion of the membrane 141 away from the rigid wall, a pocket of space is formed into which the fluid can flow. By supplying a negative pressure to the exterior surface 145 of the membrane 141, the control unit may cause more liquid to be drawn into the pressure-conduction chamber 50. Less negative pressure is needed to move the membrane 141 out of the empty-chamber position, when the actuator 149 has urged the tab 143 towards the O-ring 144 and the rigid portion 117 of the cassette adjacent the tab 143.

If it is desired to make the membrane 141 stable in the empty-chamber position, the control unit may cause the actuator 149 to be returned to the non-actuating position, so that the tab 143 may return to its normal position, extending outwardly from the cassette. As noted above, when the membrane is in the empty-chamber position, IV fluid may flow through the pressure-conduction chamber 50 through a conduit defined by raised portion of the rear wall (see FIGS. 3, 5 and 6) and leading from the inlet mouth of the pressure-conduction chamber 50 to the outlet mouth of the pressure-conduction chamber.

The pressure-reduction tab 143 also creates an instability in the filled-chamber position. When the pressure-conduction chamber 50 is filled with liquid, the exterior surface 145 of the membrane 141 becomes convex, rotating the tab 143 towards the O-ring 144, so that the tab 143 is urged against the rigid portion 117 of the cassette. In this position, the tab 143 creates pressure on a portion of the membrane 141 so as to make the membrane less stable in the filled-chamber position so that the control unit needs to create less positive pressure to collapse the membrane 141 from its filled-chamber position.

Figure 31:
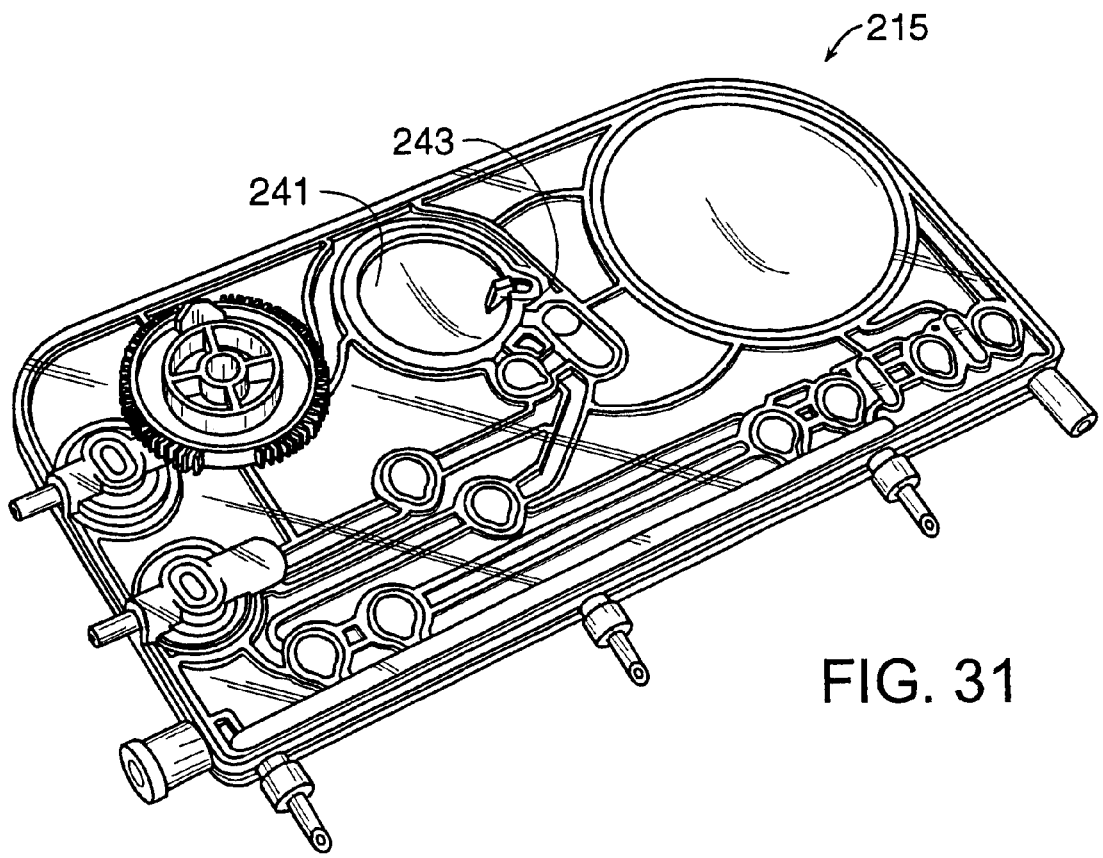
FIG. 31 shows a perspective view of an alternative cassette which may use the membrane shown in FIGS. 27–30.

FIG. 31 shows a cassette 215 that may be used in a bed-side pharmacy system, such as that described in the concurrently filed patent application for "System, Method and Cassette for Mixing and Delivering Intravenous Drugs" bearing assigned Ser. No. 08/916,890, and which lists Kamen, Grinnell, Mandro, Gilbreath, Grant, Demers, Larkins and Manning as inventors, now abandoned in favor of continuation-in-part application, assigned Ser. No. 09/137, 025 which application is incorporated herein by reference. Such a cassette may also use a membrane 241 having a pressure-reduction tab 243, which creates some instability in the filled-chamber position and which may be actuated to create some instability in the empty-chamber position.

Figure 18:
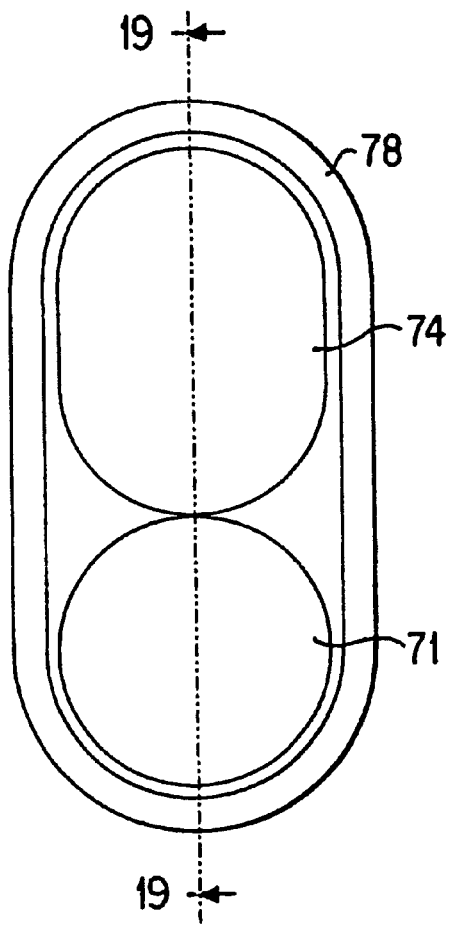
FIG. 18 shows a front view of the membrane used in the valve located downstream of the pressure-conduction chamber and upstream of the control valve.
Figure 19:
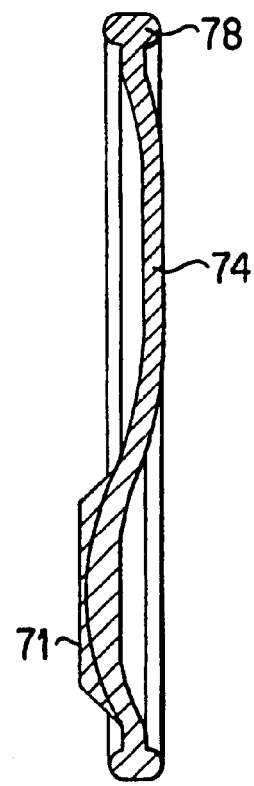
FIG. 19 shows a cross-section of the FIG. 18 membrane.

Returning to the cassette 15 shown in FIGS. 1–3, a preferred membrane design for the second membrane-based valve 7 is shown in FIGS. 18 and 19. This membrane has an O-ring 78 for mounting and sealing the inlet; membrane onto the cassette (like the lip 44 on the membrane 41 for the pressure-conduction chamber, and like the circular membrane, which is not shown, for the first membrane-based valve 6). This membrane has a first portion 71, which is used to seal off the inlet mouth 73 located on protrusion 72 (see FIG. 5). The control unit 10 exerts a pressure against this portion of the membrane 71 mechanically, in order to close off the valve 7. A second compliant portion 74 of the membrane is sufficiently compliant so that when the control valve 2 is sufficiently restricting flow out of the outlet 76 of the second membrane-based valve 7, the compliant portion 74 of the membrane will expand outwardly so as to hold, under pressure, a volume of IV fluid. This design is desirable so that when the inlet mouth 73 is closed, because the pressure-conduction chamber needs to be refilled, the fluid stored in the valving chamber (item 75 in FIG. 5) is available to be dispensed through the control valve 2.

Figure 20:
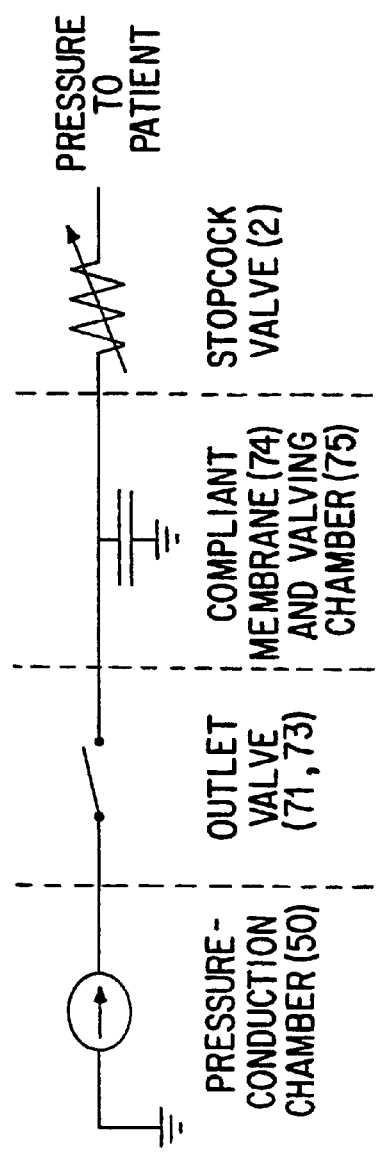
FIG. 20 is a schematic representing how the compliant membrane of FIG. 18 may be used to regulate the pressure of fluid to the patient.
Figure 21:
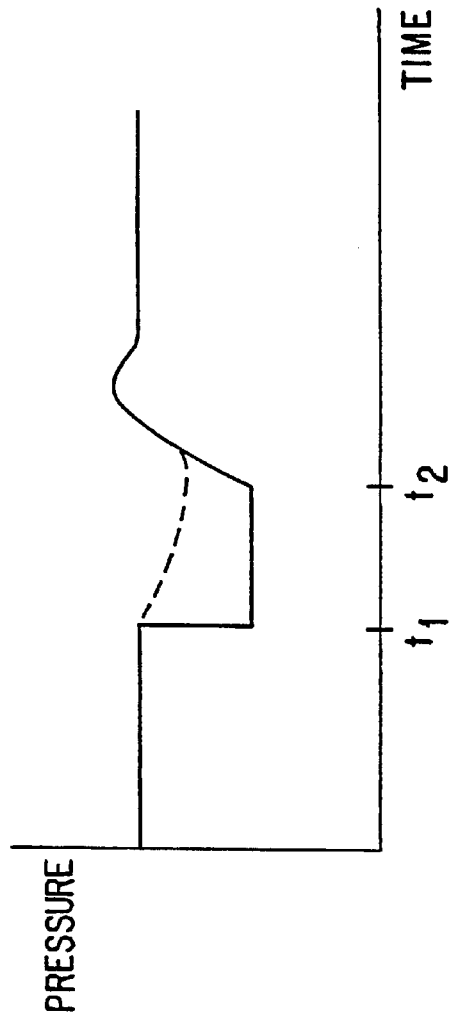
FIG. 21 is a graph depicting the advantage of using a compliant membrane such as that shown in FIG. 18.

FIG. 20 shows a schematic for an electrical model of the operation of the second membrane-based valve 7 working in conjunction with the stopcock-type control valve 20. When the valve leading from the outlet 57 of the pressure-conduction chamber 50 is open, permitting flow from the pressure-conduction chamber through valve 7, and if the stopcock valve 20 is set to provide a large amount of resistance to the flow from valve 7 to the patient, the valving chamber 75 and its corresponding compliant membrane portion 74 can accumulate a "charge" of fluid, much like a capacitor, as shown in FIG. 20. When first portion 71 is then urged against inlet mouth 73 closing off flow from the pressure-conduction chamber 50, the charge of fluid in the valving chamber 75 is urged by the compliant membrane portion 74 to continue flow through the stopcock valve 20. As fluid exits the valving chamber 75, the pressure of the fluid decreases as the compliant portion 74 of the membrane returns to its unstretched state. FIG. 21 shows a graph depicting the pressure of the IV fluid being delivered to a patient over time as outlet valve 71, 73 is closed at time $t_1$ and reopened at $t_2$. A solid line depicts the pressure to the patient without a compliant membrane portion 74 design. With a compliant membrane portion 74, the sharp drop off in pressure at $t_1$ is eliminated or ameliorated. If the stopcock valve is nearly closed so that only a small trickle of fluid is allowed to flow through it, the design of the compliant membrane portion 74 will greatly smooth out the delivery of fluid, as long as the time between $t_1$ and $t_2$ is not too long. When the stopcock valve 2 is fully open a sharp drop in pressure may still be expected at time $t_1$.

Figure 22:
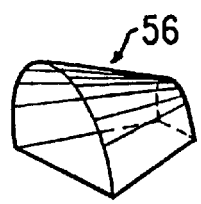
FIGS. 22 and 23 depict the preferred shape of the inlet valve to the pressure conduction chamber.
Figure 23:
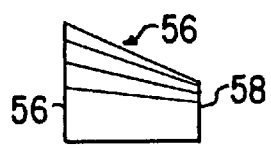
Figure 24:
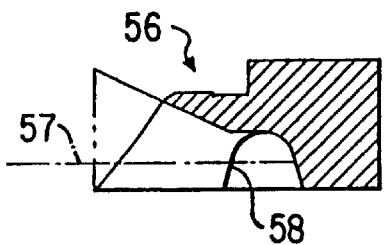
FIG. 24 shows a cross-sectional view of the inlet valve to the pressure conduction chamber.

As noted above (and as described in the above-referenced U.S. Pat. No. 5,713,865, entitled "Intravenous-Line Air-Elimination System"), when an air bubble is being purged from the pressure-conduction chamber 50, it is preferably forced up through the chamber's inlet valve 56 (which in this air-elimination mode is acting as an outlet). Preferably, the inlet port 56 is shaped so that a small bubble will not tend to stick to an edge of the port while allowing liquid to flow past it. To prevent such sticking of a small bubble, the port 56 preferably flares out so that the corner where the port 56 meets the inner wall of the pressure-conduction chamber 50 is greater than 90°, making the corner less likely a place where the bubble will stick. However, the mouth of the port 56 cannot =be so large that liquid can easily flow by the bubble when fluid is exiting the pressure-conduction through the port 56. In order to accomplish this, the port must be sized and shaped so that the surface tension of the IV fluid being forced upward from the pressure-conduction chamber 50 forces a bubble located at the port 56 up through the inlet valve 6. It is also preferable that the port 56 be sized and shaped so that when liquid is pulled back into the pressure-conduction chamber 50, the bubble can hover near the port as liquid passes around it. A preferred inlet port 56 shape is shown in FIGS. 22 and 23. The port's size increases from the end 57 that connects to the IV line's upper portion to the end 58 leading into the pressure-conduction chamber. FIG. 24 shows a cross-section of the inlet valve 56. It has been found that providing an inlet port to the pressure-conduction chamber with this shape improves the air-elimination system's ability to purge bubbles from the chamber. Using a port such as that shown in FIGS. 22–24 in conjunction with the membrane 41 of FIGS. 15–17 helps force bubbles more quickly out of the pressure-conduction chamber when attempting to purge the bubbles back through the cassette's inlet 31 to the IV source.

FIG. 25 shows a preferred arrangement of teeth around the circumference 29 of the control wheel 20. The teeth provide means for a gear in the control unit 10 to engage securely the control wheel's circumference-in particular, a gear that is used to prevent the free flow of fluid through the cassette when the cassette is removed from the control unit 10. When the door 102 of the control unit 10 is being opened, the gear turns the control wheel 20 to close the stopcock-type valve 2, thereby stopping all flow through the cassette and preventing free flow. To ensure that the gear does not continue turning the wheel 20 once the valve 2 has been closed off entirely, a sector 92 along the wheel's circumference is left free of teeth. When the wheel 20 is turned enough so that the gear is adjacent this toothless sector 92, the valve 2 is fully closed. The lack of teeth prevents the gear from continuing to turn the wheel; thus, the wheel cannot be turned too much.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A valve for smoothing the delivery of intravenous fluid from a source to a patient comprising:
   an occludable inlet mouth;
   an expandable valving chamber disposed downstream from and in fluid communication with the inlet mouth; and
   a restrictive outlet mouth disposed downstream from and in fluid communication with the expandable valving chamber, wherein the outlet mouth is capable of variably restricting delivery to the patient by providing alternatively (i) a fully open position, (ii) a partially open position and (iii) a closed position;
   so that the chamber is expandable to accept and hold under pressure a charge of fluid via the inlet mouth when the outlet mouth sufficiently restricts delivery, and so that the charge is capable of delivery to the patient when the inlet mouth is occluded, the chamber applying pressure on the charge while returning to an unstretched state such that the charge is urged to continue flowing through the outlet mouth.

2. A valve according to claim 1 further comprising:
   a compliant membrane, the membrane defining the expandable valving chamber.

3. A valve according to claim 2, wherein a portion of the compliant membrane is capable of occluding the inlet mouth.

4. A membrane-based valve for smoothing the delivery of intravenous fluid from a source to a patient comprising:

a rigid housing, the housing providing a first passage, a first mouth, a second passage, a second mouth; and a compliant membrane;

the housing and the compliant membrane coupled, defining a valving chamber; the first passage entering the valving chamber at the first mouth such that flow of fluid via the first passage into the chamber is capable of being prevented when the compliant membrane is forced against the first mouth, the second passage exiting the valving chamber at the second mouth so that a charge of fluid is capable of being urged by the compliant membrane to continue flow from the valving chamber into the second passage via the second mouth and may be provided to the patient when the compliant membrane is forced against the first mouth.

5. A valve according to claim 4, wherein the first mouth is located at an end of a protrusion provided by the rigid housing, the protrusion extending into the valving chamber towards the compliant membrane.

6. A valve comprising:

an occludable inlet mouth;

a valving chamber disposed downstream from and in fluid communication with the inlet mouth, the valving chamber capable of expanding so as to accept and retain a charge of fluid under pressure; and an outlet mouth disposed downstream from and in fluid communication with the valving chamber, so that the charge of fluid is urged, while the valving chamber is returning to its unstretched state, to flow therethrough when the inlet mouth is occluded, the outlet mouth capable of variably restricting delivery to the patient by providing alternatively (i) a fully open position, (ii) a partially open position and (iii) a closed position.

7. A valve according to claim 6, wherein the valving chamber is defined by a membrane.

8. A valve according to claim 7, wherein a portion of the membrane is capable of occluding the inlet mouth.

* * * * *